United States Patent [19]

Frincke et al.

[11] Patent Number: 5,055,289

[45] Date of Patent: Oct. 8, 1991

[54] INTERFERON ANTIBODY THERAPEUTIC COMPOSITIONS HAVING AN EXTENDED SERUM HALF-LIFE

[75] Inventors: James M. Frincke, Solana Beach; Barbara W. Unger; Karen G. Burnett, both of San Diego, all of Calif.; Evan M. Hersh, Houston, Tex.; Michael G. Rosenblum, Houston, Tex.; Jordan U. Gutterman, Houston, Tex.

[73] Assignee: Hybritech Incorporated, San Diego, Calif.

[21] Appl. No.: 234,224

[22] Filed: Aug. 19, 1988

Related U.S. Application Data

[63] Continuation of Ser. No. 732,154, filed as PCT US84/01389 on Aug 31, 1984.

[30] Foreign Application Priority Data

Sep. 1, 1983 [GB] United Kingdom ............... 8323428

[51] Int. Cl.⁵ .................... A61K 37/66; A61K 37/00
[52] U.S. Cl. .................................. 424/85.4; 424/85.8; 424/85.5; 424/85.6; 424/85.7
[58] Field of Search .................. 424/85.8, 85.4, 85.5, 424/85.6, 85.7

[56] References Cited

U.S. PATENT DOCUMENTS

| | | | |
|---|---|---|---|
| 4,093,607 | 6/1978 | Sela et al. | 424/85.8 |
| 4,520,226 | 5/1985 | Neville, Jr. | 436/548 |

OTHER PUBLICATIONS

A. Marks et al., *Molecular Immunology* 22, #3, pp. 285-290 (1985).

J. Ivanyi, *Molecular Immunology*, 19, pp. 1611-1618 (1982).

J. Ivanyi & P. Davies, *Molecular Immunology*, 17, pp. 287-290 (1980).

G. Krivi and E. Rowold, Jr., *Hybridoma*, 3, pp. 151-162 (1984).

P. A. Pontarotti et al., *Molecular Immunology*, 22, pp. 277-284 (1985).

J. D. Place et al., *Hybridoma*, 3, pp. 187-193 (1984).

M. M. Hunter et al., *J. Immunology*, 129, pp. 1165-1172 (1982).

S. Gillis and C. S. Henney, *J. Immunology*, 126, pp. 1978-1984 (1981).

A. G. Laurent et al., *Hybridoma*, 1, pp. 313-322 (1982).

L. J. Nyari et al., *Hybridoma*, 2, pp. 79-85 (1983).

C. Y. Wang et al., *Hybridoma*, 3, pp. 321-332 (1984).

Peacock, Tattersalll, Taylor, Douglas & Reeves, "Effects of New Insulins On ..." *Lancet* (1983) 1:149.

Bolli, Dimitriadis, Pehling, Baker, Haymond, Cryer, Gerich, "Abnormal Glucose ..." *N. Engl. J. Med.* (1984) 310:1706-1711.

Beythman et al., "Immunotoxin:Hybrid ...", *Nature* 290 (1981), pp. 145-146.

Masuho et al., "Importance of Antigen Antibody Binding ...", *J. Bio. Chem.* 91 (1982), pp. 1583-1591.

Raso et al., "Hybrid Antibodies with Dual Specificity ...", *Cancer Res.* 41 (1981), pp. 2073-2078.

Vitetta et al., "Immunotoxins: A New Approach To ...", *Science* 219 (1983), pp. 644-650.

*Primary Examiner*—Frederick E. Waddell
*Assistant Examiner*—Gregory Hook
*Attorney, Agent, or Firm*—June M. Bostich; Paul C. Steinhardt; Theresa A. Brown

[57] ABSTRACT

A complex of alpha-interferon with a monoclonal antibody complexes with the alpha-interferon without impairing its antiviral activity. The serum half-life of the interferon administered as the complex is substantially increased when compared to that of alpha-interferon administered alone.

19 Claims, No Drawings

INTERFERON ANTIBODY THERAPEUTIC COMPOSITIONS HAVING AN EXTENDED SERUM HALF-LIFE

This is a continuation of application Ser. No. 732,154, filed as PCT US84/01389 on Aug. 31, 1984.

FIELD OF THE INVENTION

This invention relates to therapeutically active agents and the treatment of disease therewith. In another aspect, it relates to antibody complexes of a therapeutically active agent. In a more specific aspect, it relates to complexes of a monoclonal antibody and a therapeutically active agent an their use in the treatment of disease.

BACKGROUND

It is almost a trite observation to note that the use of a broad spectrum of drugs to treat human and other mammalian disease is routine medical and veterinary practice. Therapeutically active agents, however, often suffer from a number of shortcomings which limit and complicate their use. A particular problem is that, after administration to the patient, a drug may be so rapidly cleared form the body by metabolic or other pathways or otherwise biologically inactivated so that only a relatively small percentage of the drug administered actually has a therapeutic effect. To compensate for this problem, it is common practice to increase the dosage of the drug and/or to prolong its period of administration and/or to shorten the interval between doses so that the therapeutically effective concentration of the drug in the patient is maintained for a period sufficient to achieve the desired result.

These procedures are useful but have their own limitations. Increasing the dosage may be limited, for example, in the case of intramuscular administration, by the bolus which can be tolerated. Many drugs have toxic side effects which may limit the dosage duration or interval which can be safely used. In some cases, promising drugs cannot be used because side reactions are so severe that an effective therapeutic dose cannot be safely administered. The need to administer multiple small doses of a drug or to use continuous infusion techniques increases the cost of treatment and the burden of hospital personnel, and, of course, adds to the patient's discomfort.

Accordingly, there exists a need for means by which the therapeutically active concentration of a drug, after administration, is maintained for a longer time.

SUMMARY OF THE INVENTION

It is the normal and expected function of antibodies to complex with foreign substances to more rapidly clear them from the body. We, however, have unexpectedly found that the serum or plasma half-life of a therapeutically active agent can be extended by forming a complex of the agent with a selected antibody, preferably a monoclonal antibody, which binds to the agent at a site which does not substantially impair its therapeutic activity and which extends the serum half-life of the agent. Thus, as used herein, the term "antibody" means a monoclonal antibody or polyclonal antibodies unless otherwise specified or required by the context. According to our invention, the complex of the therapeutically active agent and the antibody may be formed in vitro and then administered. Alternatively, the agent and antibody may be administered at the same time. In yet another alternative, the antibody may be administered first, and after an interval during which its distribution in the patient approaches equilibrium, the therapeutically active agent can be administered.

By selecting the proper antibody for forming the antibody: drug complex, the serum half-life and, thus, the effective concentration of the therapeutically active agent, can be maintained in vivo for a longer interval. While monoclonal antibodies are preferred for use in the invention, it is also within the scope of the invention to use polyclonal antibodies against the therapeutically active agent which complex with the therapeutically active agent without materially impairing its therapeutic activity.

Accordingly, it is an object of the present invention to provide means by which the serum half-life of a therapeutically active agent is extended.

Another object of the invention is to provide compositions which increase the effective lifetime of a therapeutic agent in vivo after administration to a patient.

DETAILED DESCRIPTION OF THE INVENTION

As indicated above, the present invention, in one embodiment, is a complex between a therapeutically active agent with a monoclonal antibody selected to bind the therapeutic agent at a site which does not materially impair its therapeutic activity but which forms a complex with the agent to confer upon the agent a serum half-life longer than that of the therapeutic agent alone and approaching the serum half-life of the antibody. Alternatively, the invention comprises a similar complex of therapeutic agent with polyclonal antibodies selected to bind the antibody without materially impairing its therapeutic activity and which form a complex having an extended serum half-life.

In another embodiment, the invention is a process involving the administration to a host of a complex comprising the therapeutic agent and either a monoclonal antibody or polyclonal antibodies having the properties noted above. The process of the present invention also includes either simultaneous administration of the therapeutics agent and a suitable antibody preparation or an initial administration of the antibody preparation followed by administration of the therapeutic agent after the antibody has had an opportunity to distribute itself throughout the host.

The therapeutic agents useful in the invention are those which are or can be made immunogenic, i.e., those for which an immune response can be obtained either directly or, in the case of a hapten, by binding the agent to a molecule which is immunogenic. Monoclonal antibodies against the therapeutic agent can be obtained by methods which are now well known to the art and which need not be described in detail. These methods generally involve immunization of a mouse or other animal species, usually mammalian or avian, with the immunogen. Human lymphoid cells may also be obtained after immunization (natural or induced)or may be sensitized in vitro. After an immune response is generated, spleen cells of the immunized mouse or other immune lymphoid cells are fused with cells of an established lymphoid tumor line using known techniques to form hybridomas which produce monoclonal antibodies. Clone of hybridomas are screened to select those which are producing monoclonal antibodies that are specific for the antigen of choice, in this case the therapeutic agent. Monoclonal antibodies having the desired specificity are further screened to select those that form an antibody:agent complex in which the agent retains all, or substantially all, of its therapeutic activity. These complexes are further screened to select those which have an extended serum half-life. In certain circumstances, it can be beneficial to use a mixture of two or more monoclonal antibodies. In some circumstances it may also be desirable to use a stoichiometric excess of antibody.

Polyclonal antibodies useful in the invention are obtained by well known techniques as well. These include stimulating an immune response against the therapeutic agent, or fragment thereof, in a suitable animal host such as a rabbit or other mammal. Chickens and other avian species can also be used. Serum taken from the host is subjected to affinity purification to isolate polyclonal antibodies against the therapeutic agent. These antibodies are subsequently fractionated, if necessary, to isolate a subpopulation which complexes with the therapeutic agent without materially impairing its desirable activity.

Particularly preferred for use in the invention are human antibodies against the therapeutic agent produced by hybridomas which, for example, are the product of fusion of a human B-lymphocyte with an established mammalian lymphoid line, e.g., a human or mouse myeloma line.

As used herein, the term antibody includes fragments thereof such as Fab, Fab', and Fab'2 or mixtures thereof and including mixtures with whole antibody. Such fractions may be less immunogenic in some patients and may also better allow better penetration of the agent to the target site.

In certain applications, the monoclonal antibody is preferably a hybrid antibody having a dual specificity, one against the therapeutically active agent and the other against another antigen, for example, an antigen associated with the disease which it is desired to treat with the agent. Among these may be mentioned tumor associated antigens such as carcinoembryonic antigen (CEA), prostatic acid phosphatase (PAP), ferritin and prostate specific antigen (PSA). In such cases, the other specificity could be selected to bind with an agent which has anti-tumor activity. For example, the second specificity could be against a toxin such as ricin or an interferon. Processes for obtaining such hybrids are described, for example, in Martinis et al., "Monoclonal Antibodies with Dual Antigen Specificity," *Protides of the Biological Fluids: Proceedings of the Thirtieth Colloquium,* 1982 311 (H. Peters ed. 1982) and in U.K. Patent No. 2,128,631 B issued to Martinis et al., which was published on May 2, 1984.

Among the therapeutic agents which are useful in the invention may be mentioned drugs such as adriamycin, vincristine, genomycin mitomycin C, and prostacyline; toxins such as abrin and ricin; and biological proteins such as the interferons (alpha, beta and gamma), the interleukins, hormones such as insulin, plasminogen activators such as urokinase, streptokinase and tissue plasminogen activator, growth factors such as nerve growth factors, and platelet activating factor. Particularly useful are complexes of a monoclonal antibody and one of the interferons, for example, alpha-interferon. As used herein, the term "interferon" is used to include those agents having the characteristics attributed to interferons as described in *Interferon: An Overview,* Ion Gresser, Ed., 4 (1982), p. 4, which is incorporated herein DNA technology which is identical to a naturally occurring interferon or which differs therefrom by one or more of the following:

1. a difference in amino acid sequence;
2. a difference in chain folding;
3. a difference in carbohydrate substitution.

The utility of the present invention is shown by the experiments described below with alpha-interferon. In that regard, alpha-interferon, a multi-species interferon, has been shown to have a therapeutic effect in the treatment of certain malignant tumors including breast cancer, multiple myeloma and malignant lymphoma. However, it has been shown to rapidly clear from the plasma of man and animals during clinical trials. This has been compensated for by giving a high dose intra-muscularly. However, the maximum dose is limited because of high-dose toxic side effects. Also, the high doses used are very expensive and may elicit an immune response in a substantial number of patients treated.

EXPERIMENTAL DETAILS

1. Preparation of anti-alpha-interferon monoclonal antibodies

Balb/c mice were immunized with partially purified leukocyte interferon. Spleen cells from immunized mice were fused with a myeloma line (either the NS-1 or SP2/0 lines) to produce hybridomas. The hybridomas were screened to select those reactive with $^{125}$I-labeled interferon in a radioimmunoassay wherein the immune complexes were removed by horse anti-mouse IgG bound to sepharose beads. Interferon used in immunization and screening were from the same source. Antibodies were selected for positive reactivity with interferon. Hybridomas producing the selected antibodies were cloned by limiting dilution to ensure homogeneity of the cell population.

2. Testing for Reactivity of an Antibody:Interferon Immune Complex in the Anti-Viral Protection Assay Approximately 40 anti-alpha interferon monoclonal antibodies were employed to make interferon:antibody immune complexes which were tested for retention of anti-viral activity using the standard method described, for example, in Rubinstein, et al., *J. Virology,* 37, 755 (1981). The first step in this procedure was formation of the immune complex by the addition of ascitic fluid to the anti-viral protection assay mixture which was monitored for inhibition of interferon activity. Ten of the forty antibodies were selected for further investigation because they did not inhibit the viral protection properties of the interferon in this assay. These anti-bodies were then further concentrated with sodium sulfate and re-tested. In each case, non-inhibition of anti-viral activity as verified. To demonstrate whether complexes of interferon with these antibodies were actually formed, the reaction mixtures were adsorbed with solid phase sepharose bound sheep anti-mouse IgG to remove the antibody and complexed interferon. The supernatant from the sepharose adsorptions were then tested in the standard antiviral protection assay. In the case of one particular antibody, designated IFG 252.2 by us, the antiviral protection was almost completely removed from the supernatent during the adsorption. Controls were performed to ensure this phenomena was not due to non-specific absorption during the sepharose absorption step. These data demonstrate that this antibody binds efficiently and avidly to interferon without inhibiting its antiviral activity.

Another known biological property of alpha interferon is its inhibition of cellular proliferation. In an assay system using DAUDI cells, retention of anti-proliferative activity was demonstrated for alpha interferon in the presence of the IFG 252.2 antibody. These data demonstrate that IFG 252.2 also binds alpha-interferon without affecting its anti-proliferative activity.

3. Administration of Alpha-Interferon:IFG 252.2 Complex to Laboratory Rats

A Fisher rat (250-260 g) was lightly anesthetized with sodium thiopental. A plastic canula was then surgically inserted into the femoral artery of the other leg. A bolus dose of alpha-interferon (Clone A of Goeddel et al., Nature, 290, 20-26 (1981), 7600 units total in 0.5 ml phosphate buffered saline) was administered over 2 seconds into the venous catheter. Blood samples (0.5 ml) were withdrawn at various times from the arterial catheter. After each blood withdrawal, 0.5 ml of PBS were injected via the venous catheter. The samples were centrifuged, the plasma decanted and analyzed for interferon anti-viral activity by standard methods. In a second rat, the same amount of interferon was preincubated with IFG 252.2 (38 microgram/microliter=190 micrograms antibody) and then administered through the venous catheter. Blood samples were taken and analyzed in the same way as for the first. The results of these experiments were then plotted and subjected to nonlinear regression analysis.

These results indicate that the activity of alpha-interferon in the rat without added anti-interferon has a two phase disappearance curve. The alpha-phase has a 6.8 minute half-life with a two log reduction of interferon activity in the plasma at 30 minutes. The volume of distribution is 20.8 ml. At 30 minutes a beta component to the plasma disappearance curve is identified with a 30 minute half-life. At two hours essentially all of the interferon activity has been lost from the plasma. The area under the curve was 7047 u/ml×min. In contrast, when the IFG 252.2 antibody is utilized to extend the half-life, a single phase disappearance of activity from plasma is observed. The half-life of this activity loss is 84 minutes. Twelve times longer than that observed for alpha-interferon itself, with a volume of distribution of 19.2 ml, essentially equivalent to that observed for alpha-interferon without added antibody. The area under the curve was 50,000 u/ml×min, seven (7) times that for the free interferon.

The foregoing experiments demonstrate that, by proper selection of an antibody, the serum half-life of a therapeutically active agent can be usefully extended without significant impairment of therapeutic activity.

Those skilled in the art will recognize that the invention, therefore, has application in veterinary medicine and for human health care. In that connection, it is within the scope of the invention to combine the therapeutic agent and/or the antibody or the antibody complex with the agent with other components such as a suitable vehicle. The foregoing description of the invention is exemplary only and modifications thereof may be made without departure from the scope of the invention which is to be limited only by the appended claims.

We claim:

1. A composition comprising a non-covalent complex of a therapeutically active agent and an antibody selected to bind said agent at a site which does not substantially impair its therapeutic activity and which extends the serum half-life of the therapeutically active agent, wherein said therapeutically active agent is an interferon.

2. A composition according to claim 1 wherein the antibody is a monoclonal antibody.

3. A composition according to claim 1 wherein the antibody comprises a population of polyclonal antibodies.

4. A composition according to claims 2 and 3 wherein the antibody comprises an antibody fragment selected from the group consisting of Fab, Fab' and Fab'2.

5. A composition according to claim 1 wherein the antibody is a hybrid monoclonal antibody having a dual specificity one of which is against the therapeutically active agent and the other against a disease associated antigen.

6. A composition according to claim 5 wherein the hybrid antibody is an antibody fragment selected from Fab, Fab' and Fab'2.

7. A composition according to claim 1 wherein the interferon is selected from alpha, beta and gamma interferons.

8. A composition according to claims 5 or 6 wherein one specificity of the hybrid antibody is directed against a tumor associated antigen and the other against the agent having anti-tumor activity.

9. A composition according to claim 8 wherein the tumor associated antigen is selected from CEA, PAP, PSA, or ferritin.

10. A composition according to claim 1, 2, 3 or 5 further comprising a pharmaceutical vehicle.

11. A method for treating viral diseases and tumors in an animal comprising parenterally administering thereto an effective amount of a therapeutically active agent and an antibody against said agent which binds the agent noncovalently at a site which does not substantially impair its therapeutic activity and which extends the serum half-life of the agent, wherein said therapeutically active agent is an interferon.

12. A method of claim 11 wherein the antibody and agent are combined in vitro.

13. A method of claim 11 wherein the antibody and agent are separately administered.

14. A method of claim 13 wherein the antibody is allowed to distribute itself throughout the patient prior to administration of the agent.

15. A method of claims 11, 12, 13 or 14 wherein the antibody is a monoclonal antibody.

16. A method of claim 15 wherein the monoclonal antibody is a hybrid antibody having a dual specificity one of which is directed against the therapeutically active agent and the other against a disease associated antigen.

17. A method of claim 15 wherein the antibody is a fragment selected from Fab, Fab' and Fab'2.

18. A method of claim 11 wherein the interferon is selected from alpha, beta and gamma interferons.

19. A method of claim 16 wherein the antigen is a tumor associated antigen and the agent has anti-tumor activity.

* * * * *